United States Patent [19]

Lantz et al.

[11] Patent Number: 4,791,223

[45] Date of Patent: Dec. 13, 1988

[54] PROCESS FOR THE PREPARATION OF 1,1,2,2-TETRAHYDROPERFLUOROALKANOLS AND THEIR ESTERS

[75] Inventors: André Lantz, Vernaison; Pascal Michaud, La Mulatiere, both of France

[73] Assignee: Societe Atochem, Puteuax, France

[21] Appl. No.: 128,825

[22] Filed: Dec. 4, 1987

[30] Foreign Application Priority Data

Dec. 22, 1986 [FR] France ................................ 86 17983

[51] Int. Cl.⁴ .............................................. C07C 67/02
[52] U.S. Cl. .................................. 560/266; 560/236; 260/410.9 R
[58] Field of Search ............................. 560/236, 266; 260/410.9 R

[56] References Cited

U.S. PATENT DOCUMENTS 3,239,557  8/1966  Fasick ................................. 560/266
3,979,469  9/1976  Jager .................................. 560/266

FOREIGN PATENT DOCUMENTS 9141538  8/1984  Japan ................................. 560/266

OTHER PUBLICATIONS

Matsuo, M. et al, Asahi Garasu Kenkyu Hokoku 26(1) 55-61, 1976.
Dieng, S. Y. et al., J. Fluorine Chem. 28(3) 341-55, 1985.

*Primary Examiner*—Paul J. Killos
*Attorney, Agent, or Firm*—Stevens, Davis, Miller & Mosher

[57] ABSTRACT

The invention relates to the synthesis of 1,1,2,2-tetrahydroperfluoroalkanols and their esters by oxidizing a 2-(perfluoroalkyl)ethyl iodide using hydrogen peroxide in a carboxylic acid or carboxylic acid ester in the presence of sulphuric acid.

In the process according to the invention, from 1 to 30 moles of sulphuric acid, from 1 to 50 moles of carboxylic acid or of an ester of such an acid, and from 3 to 20 moles of hydrogen peroxide per mole of 2-perfluoralkyl)ethyl iodide are used.

8 Claims, No Drawings

PROCESS FOR THE PREPARATION OF 1,1,2,2-TETRAHYDROPERFLUOROALKANOLS AND THEIR ESTERS

FIELD OF THE INVENTION

The present invention relates to the synthesis of 1,1,2,2-tetrahydroperfluoroalkanols ($R_FCH_2CH_2OH$) and their esters by oxidizing the corresponding 2-(perfluoroalkyl)-ethyl iodides ($R_FCH_2CH_2I$) using hydrogen peroxide. The perfluoroalkyl radical $R_F$ may contain from 1 to 20 carbon atoms and may be straight-chain or branched chain.

BACKGROUND OF THE INVENTION

These polyfluorinated alcohols and esters are valuable intermediates of the production of surface-active agents and hydrophobic and oleophobic substances. In particular they may easily be converted into acrylic or methacrylic esters. The polymerization of these esters optionally with other monomers, gives hydrophobic and oleophobic finishing agents for textile materials, leather, paper or other substrates. Alcohol and ester mixtures may also be converted entirely into alcohols.

Several processes for the preparation of these polyfluorinated alcohols and esters are known. The process described in French Pat. No. 1,380,579 relates to reacting an iodide $R_FCH_2CH_2I$ with fuming sulphuric acid and then to hydrolyzing the sulphate formed. It has the disadvantage of producing large quantities of sulphuric diesters. These diesters are difficult to hydrolyze. The patent is hereby incorporated by reference.

According to the process described in U.S. Pat. No. 3,239,557, it is possible to obtain the esters $R_FCH_2CH_2OCOR$ by reacting an iodide $R_FCH_2CH_2I$ with a salt of a carboxylic acid RCOOH. However, the yields are not very high because variable quantities of the olefin $R_FCH=CH_2$ are formed. The patent is hereby incorporated by reference.

The alcohols $R_FCH_2CH_2OH$ may also be obtained according to the process of French Pat. No. 2,096,179, hereby incorporated by reference, which relates to preparing the nitrates $R_FCH_2CH_2ONO_2$ by reacting the iodides $R_FCH_2CH_2I$ with nitric acid and to hydrogenating these nitrates into alcohol. However, this process has the disadvantage of requiring two reaction stages, the latter of which must be carried out under a high hydrogen pressure.

The French Pat. No. 2,180,113, hereby incorporated by reference, describes a process for the production of mixtures of alcohols $R_FCH_2CH_2OH$ and formates $R_FCH_2CH_2OCOH$ by reacting the iodides $R_FCH_2CH_2I$ with dimethylformamide at high temperature in the presence of a small quantity of water. This process has the disadvantage of requiring very harsh reaction conditions and of producing the olefin $R_FCH=CH_2$ as by-product. This reduces the yield accordingly. Additionally, a good selectivity for alcohol and formate can only be obtained by using very large quantities of dimethylformamide.

More recently, the preparation of these polyfluorinated alcohols and esters by reacting the iodide $R_FCH_2CH_2I$ with a peroxoacid $RCO_3H$ which has previously been formed by adding hydrogen peroxide to a carboxylic acid $RCO_2H$ in the presence or otherwise of a small quantity of sulphuric acid has been proposed in European Pat. No. 24,224 and West Germany Pat. No. 3,035,641. However, under the operating conditions described, this process leads to the production of the olefin by-product $R_FCH=CH_2$ in a significant quantity and/or to a low conversion rate for the iodide $R_FCH_2CH_2I$. The patents are hereby incorporated by reference.

A process which enables these disadvantages to be overcome, that is, the production of the olefin by-product $R_FCH=CH_2$ is prevented and a very high conversion rate is obtained, has now been discovered.

SUMMARY OF THE INVENTION

The process according to the invention comprises oxidizing a 2-(perfluoroalkyl)ethyl iodide using hydrogen peroxide in a carboxylic acid or an ester of such an acid and in the presence of sulphuric acid. The process uses from 1 to 30 moles of sulphuric acid (preferably from 3 to 10 moles), from 1 to 50 moles of carboxylic acid or of an ester of such an acid (preferably from 5 to 15 moles), and from 3 to 20 moles of hydrogen peroxide (preferably 5 to 6 moles) all per mole of 2-(perfluoroalkyl)ethyl iodide.

DETAILED DESCRIPTION

Hydrogen peroxide is advantageously used in the form of aqueous solutions. The $H_2O_2$ concentration of the solution varies from approximately 35 to 75% by weight and is preferably between 65 and 75%.

Although it is preferable to use pure or very concentrated (80% by weight or higher) sulphuric acid, it is also possible to use sulphuric acid solutions containing up to 50% by weight of water.

As carboxylic acids, aliphatic acids which are liquids under the operating conditions are preferably used. These acids which generally contain from 1 to 8 carbon atoms may be straight-chain or branched chain, saturated or unsaturated, and may contain substituents such as, for example, halogen atoms. Acetic acid and propionic acid are particularly useful.

It is also possible to use solid carboxylic acids such as higher aliphatic acids or aromatic acids (for example benzoic acid and its substituted derivatives) by adding a solvent such as an alcohol (for example methanol, ethanol or propanol) or an ester.

As mentioned above, a carboxylic acid ester may be used. This ester is preferably an ester of an aliphatic alcohol containing 1 to 4 carbon atoms, for example ethyl acetate, butyl acetate or ethyl propionate.

The oxidation according to the invention may be carried out at a temperature which may range from $-20°$ to $140°$ C., but which is advantageously between $60°$ and $90°$ C.

The process according to the invention may be carried out in different ways. For example, it is possible to operate, as in European Pat. No. 24,224 and West German Pat. No. 3,035,641 by adding to the 2-(perfluoroalkyl)ethyl iodide a mixture of hydrogen peroxide, sulphuric acid and carboxylic acid or the ester in the required proportions. It is also possible to operate in the reverse manner by introducing the iodide into such a mixture.

However, the preferred embodiment of the invention comprises introducing hydrogen peroxide into a mixture of 2-(perfluoroalkyl)ethyl iodide, sulphuric acid and the carboxylic acid or the carboxylic acid ester. This introduction is advantageously carried out under vigorous stirring. The addition rate is such that the temperature of the reaction medium is maintained by itself between 60° and 90° C.

The reaction is generally very quick and takes place with a release of iodine and/or of iodic acid which can easily be separated from the reaction mixture by filtration. The major portion of iodine may thus be recovered in the form of elementary iodine by treating the iodic acid with a conventional reducing agent such as sodium sulphite.

The fluorinated products may be isolated according to conventional methods, for example by phase separation and washing the organic phase with water. A product which mainly comprises the 2-(perfluoroalkyl)ethyl ester ($R_FC_2H_4OCOR$) is finally obtained. The ester may be saponified to obtain the alcohol $R_FCH_2CH_2OH$ or be converted into another ester, epecially into acrylate or methacrylate.

As it has already been pointed out in the above-cited German Pat. No. 3,035,641, working with peracids and hydrogen peroxide involves not-negligible risks of firing and explosion. Consequently, when carrying out the process according to this invention, it is urged to take all the usual security measures against these risks.

EXAMPLES

The following examples in which the percentages refer to percentages by weight, illustrate the invention without limiting it.

EXAMPLE 1

47.4 g (0.1 mole) of 2-(perfluorohexyl)ethyl iodide, 60 g of acetic acid and 28 ml of 98% sulphuric acid are charged into a 250 ml glass reactor equipped with a high power stirrer, a reflux condenser and a dropping funnel, 24.7 g of a 70% hydrogen peroxide solution (which amounts to 0.5 mole of $H_2O_2$) are then added dropwise during a 50 minute period. The temperature rises by itself to 75°–80° C. and is maintained at this level for a further period of 30 to 45 minutes following the completion of the addition.

The reaction mixture is then filtered to separate the iodine and the iodic acid formed and phase separation of the filtrate is then carried out. The organic phase is washed with 3×50 ml of water at 25° C.

38 g of organic phase are thus obtained. The distribution of fluorinated compounds, as determined by chromatography, is as follows:
95% of $C_6F_{13}C_2H_4OCOCH_3$,
3.1% of $C_6F_{13}C_2H_4OH$,
1.5% of $(C_6F_{13}C_2H_4O)_2SO_2$, and
1.4% of unconverted $C_6F_{13}C_2H_4I$.

EXAMPLE 2

47.4 g of 2-(perfluorohexyl)ethyl iodide, 30 ml of 98% sulphuric acid and 74 g of propionic acid are charged into a reactor identical to that in Example 1. 26.9 g of a 70% hydrogen peroxide solution are then added dropwise during a 45 minute period. The mixture is maintained at 75°–80° C. for a further period of 30 minutes with stirring.

After filtering, phase separation of the filtrate and washing with sodium sulphite and with water, 40 g of organic phase are recovered. The distribution of fluorinated compounds is as follows:
98.4% of $C_6F_{13}C_2H_4OCOC_2H_5$,
1.49% of $C_6F_{13}C_2H_4OH$, and
0.2% of unconverted $C_6F_{13}C_2H_4I$.

EXAMPLE 3

Operating as in Example 2, starting with 37.4 g of 2-(perfluorobutyl)ethyl iodide, 28 g of organic phase are obtained. The distribution of fluorinated compounds is as follows:
97% of $C_4F_9C_2H_4OCOC_2H_5$,
1.5% of $C_4F_9C_2H_4OH$, and
1.5% of unconverted $C_4F_9C_2H_4I$.

EXAMPLE 4

The reaction is carried out as in Example 2, but replacing the 2-(perfluorohexyl)ethyl iodide by 53.8 g of a mixture of iodides $R_FC_2H_4I$ having the following composition by weight:

| $R_F$ | % |
|---|---|
| $C_6F_{13}$ | 56.1 |
| $C_8F_{17}$ | 25.0 |
| $C_{10}F_{21}$ | 10.1 |
| $C_{12}F_{25}$ | 4.0 |
| $\geq C_{14}F_{29}$ | 4.8 |

The average molecular weight of this mixture is in the vicinity of 538.

The distribution of fluorinated compounds in the organic phase thus obtained (40 g) is as follows:
97.8% of $R_FC_2H_4OCOC_2H_5$,
2% of $R_FC_2H_4OH$, and
0.2% of unconverted $R_FC_2H_4I$.

EXAMPLE 5

Operating as in Example 2, starting with 27.4 g of 3,3,4,4,4-pentafluorobutyl iodide, 20 g of organic phase are obtained. The fluorinated compounds are distributed as follows:
96.5% of $C_2F_5C_2H_4OCOC_2H_5$,
1.5% of $C_2F_5C_2H_4OH$, and
2% of unconverted $C_2F_5C_2H_4I$.

EXAMPLE 6

47.4 g of 2-(perfluorohexyl)ethyl iodide, 30 ml of 98% sulphuric acid and 163 g of trichloroacetic acid are charged into a reactor identical to that in Example 1. 26.9 g of a 70% hydrogen peroxide solution are then added, with stirring, at an addition rate such that the temperature is maintained at 70°–80° C. When the addition of hydrogen peroxide is complete, the mixture is maintained stirred for a further period of 30 minutes.

After cooling to 20° C., 100 ml of water are added. 12.3 g of crude iodine are recovered by filtration. After phase separation of the filtrate and washing the organic phase with water, 53 g of a product are obtained. The distribution of fluorinated compounds is as follows:
90.6% of $C_6F_{13}C_2H_4OCOCCl_3$,
1.1% of $C_6F_{13}C_2H_4OH$,
5.6% of $(C_6F_{13}C_2H_4O)_2SO_2$, and
2.7% of unconverted $C_6F_{13}C_2H_4I$.

EXAMPLE 7

The reaction is carried out as in Example 2, but replacing the 74 g of propionic acid by 144 g of octanoic acid. 56 g of organic phase are obtained. The fluorinated compounds are distributed as follows:
98% of $C_6F_{13}C_2H_4OCOC_7H_{15}$,
0.8% of $C_6F_{13}C_2H_4OH$, and
1.2% of unconverted $C_6F_{13}C_2H_4I$.

EXAMPLE 8

The reaction is carried out as in Example 2, but replacing the propionic acid by 88 g of ethyl acetate. 38 g of organic phase are thus obtained. The fluorinated compounds are distributed as follows:

79.3% of $C_6F_{13}C_2H_4OCOCH_3$,
18.2% of $C_6F_{13}C_2H_4OH$, and
2.5% of unconverted $C_6F_{13}C_2H_4I$.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A process for the preparation of 1,1,2,2-tetrahydroperfluoroalkanols and their esters comprising oxidizing a 2-(perfluoroalkyl)ethyl iodide using hydrogen peroxide in a carboxylic acid or an ester of such an acid and in the presence of sulphuric acid, and using from 1 to 30 moles of sulphuric acid, from 1 to 50 moles of carboxylic acid or of an ester of such an acid, and from 3 to 20 moles of hydrogen peroxide, all per mole of 2-(perfluoroalkyl)ethyl iodide.

2. The process according to claim 1, further comprising using 3 to 10 moles of sulphuric acid, 5 to 15 moles of carboxylic acid or of an ester of such an acid, and 5 to 6 moles of hydrogen peroxide, all per mole of 2-(perfluoroalkyl)ethyl iodide.

3. The process according to claim 1, further comprising carrying out the reaction at a temperature from 60° to 90° C.

4. The process according to claim 1, further comprising introducing hydrogen peroxide into a solution containing 2-(perfluoroalkyl)ethyl iodide, carboxylic acid or an ester of such an acid, and sulphuric acid.

5. The process according to claim 1, further comprising using hydrogen peroxide in the form of an aqueous solution, the $H_2O_2$ concentration of which may vary from 35 to 75% by weight.

6. The process according to claim 5, further comprising a $H_2O_2$ concentration between 65 and 75% by weight.

7. The process according to claim 1, further comprising using sulphuric acid, which is pure or diluted, with up to 50% by weight of water.

8. The process according to claim 1, further comprising using acetic or propionic acid.

* * * * *